United States Patent
Lee et al.

(10) Patent No.: US 10,626,072 B2
(45) Date of Patent: Apr. 21, 2020

(54) METHOD OF PREPARING METHYL TERT-BUTYL ETHER

(71) Applicant: LG CHEM, LTD., Seoul (KR)

(72) Inventors: Sung Ho Lee, Daejeon (KR); Sang Beom Lee, Daejeon (KR); Joon Ho Shin, Daejeon (KR); In Yong Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/073,294

(22) PCT Filed: Jan. 4, 2018

(86) PCT No.: PCT/KR2018/000155
§ 371 (c)(1),
(2) Date: Jul. 26, 2018

(87) PCT Pub. No.: WO2018/128402
PCT Pub. Date: Jul. 12, 2018

(65) Prior Publication Data
US 2019/0315671 A1    Oct. 17, 2019

(30) Foreign Application Priority Data

Jan. 6, 2017 (KR) .................. 10-2017-0002605
Jan. 3, 2018 (KR) .................. 10-2018-000673

(51) Int. Cl.
*C07C 41/06* (2006.01)
*B01D 3/00* (2006.01)
(Continued)

(52) U.S. Cl.
CPC .............. *C07C 41/06* (2013.01); *B01D 3/009* (2013.01); *B01J 39/05* (2017.01); *B01J 39/20* (2013.01);
(Continued)

(58) Field of Classification Search
CPC .......... C07C 41/06; C07C 41/42; B01D 3/009
See application file for complete search history.

(56) References Cited

U.S. PATENT DOCUMENTS 3,979,461 A    9/1976 Ancillotti et al.
4,404,409 A    9/1983 Fujiwara et al.
(Continued)

FOREIGN PATENT DOCUMENTS

EP    0071238        9/1986
EP    0071238 B1     9/1986
(Continued)

OTHER PUBLICATIONS

Supplementary Search Report of European Patent Office in Appl'n No. EP18736760, dated Mar. 11, 2019.

*Primary Examiner* — Rosalynd A Keys
(74) *Attorney, Agent, or Firm* — Dentons US LLP

(57) ABSTRACT

The present invention relates to a method of preparing methyl tert-butyl ether including a reaction step of reacting methanol with iso-butene in the presence of an acid catalyst to generate methyl tert-butyl ether; and a purification step of purify the reaction product obtained by the reaction step by introducing the reaction product into a reaction distillation column including a packing stage containing an acid catalyst, wherein a flow ratio of a recycle to a fresh feed is different per the volume of each reactor. Accordingly, the amount of unreacted iso-butene and the amount of impurities included in the reactor may be reduced, resulting in reduction of the amount of thermal energy used in a reaction distillation column.

14 Claims, 2 Drawing Sheets

(51) Int. Cl.
    *C07C 41/42*     (2006.01)
    *B01J 39/20*     (2006.01)
    *B01J 39/05*     (2017.01)

(52) U.S. Cl.
    CPC ....... *C07C 41/42* (2013.01); *B01J 2219/0004* (2013.01); *B01J 2219/00038* (2013.01)

(56) References Cited

U.S. PATENT DOCUMENTS

| | | |
|---|---|---|
| 5,789,627 A | 8/1998 | Hwan et al. |
| 6,657,090 B2 | 12/2003 | Rix et al. |
| 2007/0203369 A1* | 8/2007 | Praefke .................... C07C 7/04 568/690 |

FOREIGN PATENT DOCUMENTS

| | | |
|---|---|---|
| JP | S55-118431 | 9/1980 |
| JP | S58-026833 | 2/1983 |
| JP | S60-058932 | 4/1985 |
| JP | H06199722 | 7/1994 |
| JP | H09110769 | 4/1997 |
| JP | 2002179603 | 6/2002 |
| KR | 10-1983-0002476 | 10/1983 |
| KR | 10-0853947 | 8/2008 |

* cited by examiner

METHOD OF PREPARING METHYL TERT-BUTYL ETHER

CROSS-REFERENCE TO RELATED APPLICATIONS

This application is a National Stage Application of International Application No. PCT/KR2018/000155 filed on Jan. 4, 2018, which claims priority to and the benefit of Korean Patent Application No. 10-2017-0002605, filed on Jan. 6, 2017, and Korean Patent Application No. 10-2018-0000673, re-filed on Jan. 3, 2018 claiming the benefit of priority based on Korean Patent Application No. 10-2017-0002605, in the Korea Intellectual Property Office, the disclosure of each of which is incorporated herein in its entirety by reference for all purposes as if fully set forth herein.

TECHNICAL FIELD

The present invention relates to a method of preparing methyl tert-butyl ether. More specifically, the present invention relates to a method of preparing methyl tert-butyl ether capable of reducing the amount of thermal energy used in a reaction distillation column by reducing the amount of unreacted iso-butene and the amount of impurities contained in a reactor.

BACKGROUND ART

Methyl tertiary-butyl ether (MTBE), which is a compound produced by the reaction of iso-butene-type olefins with methanol, contains oxygen atoms in a molecular structure thereof. Accordingly, MTBE is mixed with gasoline to reduce the generation of nitrogen oxides, carbon monoxide, and the like. In addition, MTBE has a very high octane number of about 118, which is also useful for improving the octane number of gasoline.

MTBE may be produced by reacting methanol with iso-butene in the presence of an acid catalyst. As this reaction is an equilibrium reaction, general reactors are not suitable. Accordingly, a distillation column is installed at a rear end of a reactor to overcome equilibrium reaction, thereby producing MTBE products.

However, since the amount of thermal energy used in the distillation column is too high, there is a need for development of technology to reduce use of thermal energy.

PRIOR ART DOCUMENT

[Patent Document] KR 10-0853947 B1

DISCLOSURE

Technical Problem

Therefore, the present invention has been made in view of the above problems, and it is one object of the present invention to provide a method of preparing methyl tert-butyl ether capable of reducing the amount of thermal energy used in a reaction distillation column by reducing the amount of unreacted iso-butene and the amount of impurities contained in a reactor.

The above and other objects can be accomplished by the present disclosure described below.

Technical Solution

In accordance with one aspect of the present invention, provided is a method of preparing methyl tert-butyl ether, the method including a reaction step of reacting methanol with iso-butene in the presence of an acid catalyst to generate methyl tert-butyl ether; and a purification step of purify the reaction product obtained by the reaction step by introducing the reaction product into a reaction distillation column including a packing stage containing an acid catalyst, wherein the reaction step is performed in a first reaction part including one reactor or two or more reactors connected in parallel; and in a second reaction part including one or more reactors connected in series to the first reaction part, wherein a portion of a reaction product discharged from the first reaction part is recycled in the first reaction part, wherein a flow ratio of a recycle to a fresh feed is greater than 0.9 and less than 1.7 when a total volume of the one or more reactors included in the first reaction part is 30 $m^3$ or less, a flow ratio of a recycle to a fresh feed is greater than 2.2 and less than 4.8 when a total volume of the one or more reactors included in the first reaction part is greater than 30 $m^3$ and 60 $m^3$ or less, and a flow ratio of a recycle to a fresh feed is greater than 3.1 and less than 9.8 when a total volume of the one or more reactors included in the first reaction part is greater than 60 $m^3$.

Advantageous Effects

As apparent from the foregoing, the present invention advantageously provides a method of preparing methyl tert-butyl ether capable of reducing the amount of thermal energy used in a reaction distillation column by reducing the amount of unreacted iso-butene and the amount of impurities contained in a reactor.

BEST MODE

Figure 1:
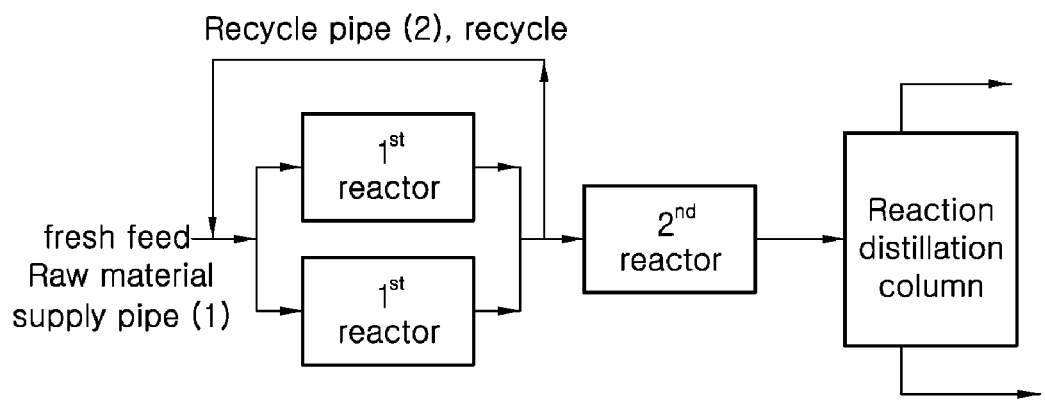
FIG. 1 is a block diagram schematically illustrating process operation of an apparatus wherein a first reaction part including two reactors connected in parallel and a second reaction part including one reactor are connected in series according to an embodiment of the present invention.

Hereinafter, a method of preparing methyl tert-butyl ether of the present invention is described in detail.

The present inventors confirmed that, when a residence time of a product in reactors and the composition of the product at inlets of the reactors are controlled in predetermined ranges by additionally installing the reactors in parallel and changing a flow rate of the product discharged from the reactors and recycled, a section in which a conversion rate to iso-butene increases and the amount of impurities is reduced is generated. Based on these findings, the present inventors have completed the present invention.

The method of preparing methyl tert-butyl ether of the present invention includes, for example, a reaction step of reacting methanol with iso-butene in presence of an acid catalyst to generate methyl tert-butyl ether; and a purification step of purify the reaction product obtained by the reaction step by introducing the reaction product into a reaction distillation column including a packing stage containing an acid catalyst, wherein the reaction step is performed in a first reaction part including one reactor or two or more reactors connected in parallel; and in a second reaction part including one or more reactors connected in series to the first reaction part, wherein a portion of a reaction product discharged from the first reaction part is recycled in the first reaction part, wherein a flow ratio of a recycle to a fresh feed is greater than 0.9 and less than 1.7 when a total volume of the one or more reactors included in the first reaction part is 30 m$^3$ or less, a flow ratio of a recycle to a fresh feed is greater than 2.2 and less than 4.8 when a total volume of the one or more reactors included in the first reaction part is greater than 30 m$^3$ and 60 m$^3$ or less, and a flow ratio of a recycle to a fresh feed is greater than 3.1 and less than 9.8 when a total volume of the one or more reactors included in the first reaction part is greater than 60 m$^3$.

A reaction step causing equilibrium formation is as follows:

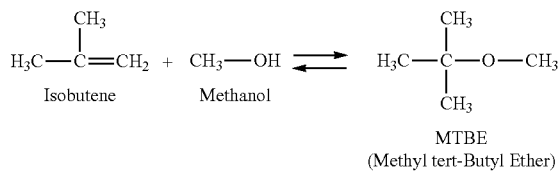

The iso-butene may be, for example, a mixture of C4-hydrocarbons including iso-butene. The mixture of C4-hydrocarbons may include, other than iso-butene, n-butane, iso-butane, butene-1, butene-2, butadiene, and the like. For example, a C4 hydrocarbon fraction obtainable by pyrolysis, stream cracking, catalytic decomposition, etc. of petroleum may be effectively used.

As the methanol, for example, a commercially available product may be used, but it is preferred to use methanol having a water content of less than 1% by weight.

As the methanol, for example, methanol having a purity of 99.9% or more may be used. Methanol may be introduced to the one or more reactors through a separate pipe.

The acid catalyst may be used without specific limitation so long as it is generally used in the technical field.

The one or more reactors may include, for example, an acid catalyst in an amount of 200 to 1200 kg, or 300 to 1000 kg, preferably 300 to 800 kg, for a reactor unit volume (m$^3$) of each thereof. Within these ranges, a conversion rate to iso-butene increases and the amount of impurities is reduced, whereby a reflux amount in the reaction distillation column is decreased. As a result, the amount of thermal energy used in the reaction distillation column may be reduced.

Preferably, the one or more reactors included in each of the first and second reaction parts are charged with the same amount of an acid catalyst per unit volume (m$^3$) of each of the reactors. In this case, the amount of thermal energy used in the reaction distillation column may be reduced.

For example, since the acid catalyst has high selectivity for formation of an iso-butene oligomer and a small amount of by-products is produced, it is preferred to use an acid ion exchange resin.

The acid ion exchange resin may be an acid ion exchange resin generally used in generation reaction of methyl tert-butyl ether (MTBE). For example, the acid ion exchange resin may be prepared by sulfonation of a phenol/aldehyde condensate or a co-oligomer of an aromatic vinyl compound. The aromatic vinyl compound used to prepare the co-oligomer may be, for example, one or more selected from the group consisting of styrene, vinyltoluene, vinyl-naphthalene, vinylethylbenzene, methylstyrene, vinylchloro-benzene, vinylxylene, and divinyl benzene.

The acid ion exchange resin may be prepared, for example, in a gel form or a sponge shape or to have macro-pores. The characteristics, particularly specific surface area, porosity, stability, swelling or shrinkage, and exchange capacity, of the resin, may be adjusted by a preparation process.

The fresh feed of the present invention may be a feed that has not been recycled and is first supplied to the first reaction part. For example, the fresh feed may refer to a pure feed stream that includes a mixture of C4-hydrocarbon containing iso-butene.

The fresh feed fed into the first reaction part may include, for example, a mixture of C4-hydrocarbons including 20 to 60% by weight or 30 to 60% by weight, preferably 40 to 55% by weight of iso-butene. Within these ranges, a conversion rate to iso-butene may increase and high-purity methyl tert-butyl ether may be produced.

The mixture of C4-hydrocarbon may include, for example, a mixture including propane, propene, iso-butane, iso-butene, 1-butene, 1,3 butadiene, 1,2 butadiene, n-butane, tert-2-butene, cis-2-butene, or C5 hydrocarbons.

The expression "recycle," used in the present invention may refer to a stream discharged after passing through the first reaction part at least once, particularly a stream, a portion of which present between the first reaction part and the second reaction part is recycled in the first reaction part.

The recycle may refer to, for example, a stream that includes a mixture of C4-hydrocarbons containing iso-butene, methanol, and methyl tert-butyl ether and is recycled.

The recycle fed into the first reaction part may include, for example, 1 to 20% by weight, 3 to 10% by weight, or 2 to 5% by weight of iso-butene; 1 to 20% by weight or 1 to 11% by weight, preferably 2 to 5% by weight of methanol; and 20 to 60% by weight or 24 to 50% by weight, preferably 45 to 50% by weight, of methyl tert-butyl ether. Within these ranges, a conversion rate to iso-butene may be increased and the amount of impurities may be reduced.

The first reaction part may include, for example, one reactor or two or more reactors connected in parallel.

As a particular example, the first reaction part may include, for example, one reactor or two or three reactors connected in parallel.

A flow ratio of the recycle to the fresh feed fed into the first reaction part may depend upon a total volume of the one or more reactors included in the first reaction part.

For example, a flow ratio of a recycle to a fresh feed may be greater than 0.9 and less than 1.7 when a total volume of the one or more reactors included in the first reaction part is 30 m$^3$ or less, a flow ratio of a recycle to a fresh feed may be greater than 2.2 and less than 4.8 when a total volume of the one or more reactors included in the first reaction part is greater than 30 m$^3$ and 60 m$^3$ or less, and a flow ratio of a recycle to a fresh feed may be greater than 3.1 and less than 9.8 when a total volume of the one or more reactors included in the first reaction part is greater than 60 m$^3$. Within these ranges, a conversion rate to iso-butene may increase and the amount of impurities may be reduced, whereby a reflux amount in the reaction distillation column may be reduced. As a result, the amount of thermal energy used in the reaction distillation column may be reduced.

As a particular example, when a total volume of the one or more reactors included in the first reaction part is 30 $m^3$ or less, or 25 $m^3$ to 30 $m^3$, a flow ratio of a recycle to a fresh feed may be 1.0 to 1.6 or 1.1 to 1.5, preferably 1.3 to 1.5. Within these ranges, the amount of thermal energy used in the reaction distillation column may be reduced.

When a total volume of the one or more reactors included in the first reaction part is greater than 30 $m^3$ and 60 $m^3$ or less, or 50 $m^3$ to 60 $m^3$, a flow ratio of a recycle to a fresh feed may be, for example, 2.4 to 6.2 or 2.5 to 5.0. The flow ratio is preferably 2.6 to 3.1. Within these ranges, the amount of thermal energy used in the reaction distillation column may be reduced.

When a total volume of the one or more reactors included in the first reaction part is greater than 60 $m^3$, or 80 $m^3$ to 100 $m^3$, or 80 $m^3$ to 90 $m^3$, for example, a flow ratio of a recycle to a fresh feed may be 2.5 to 6.5, or 3.1 to 6.5. The flow ratio is preferably 4.8 to 6.2. Within these ranges, the amount of thermal energy used in the reaction distillation column may be reduced.

When a total volume of the one or more reactors included in the first reaction part is greater than 60 $m^3$ to 150 $m^3$, or greater than 60 $m^3$ to 125 $m^3$, or greater than 60 $m^3$ to 100 $m^3$, a flow ratio of a recycle to a fresh feed may be, for example, 2.5 to 6.5, or 3.1 to 6.5, preferably 4.8 to 6.2. Within these ranges, the amount of thermal energy used in the reaction distillation column may be reduced.

As another example, when the first reaction part includes one reactor, a flow ratio of a recycle to a fresh feed may be 1.1 to 9.8. The flow ratio is preferably 1.1 to 6.5 and more preferably 1.2 to 6.2. Within these ranges, the amount of thermal energy used in the reaction distillation column may be reduced. Here, the volume of the reactor may be 10 to 120 $m^3$ or 20 to 105 $m^3$. The volume is preferably 25 to 105 $m^3$.

For example, when the first reaction part includes two reactors connected in parallel, a flow ratio of a recycle to a fresh feed may be greater than 2.2 and less than to 9.8, or 2.3 to 6.5. The flow ratio is preferably 2.4 to 6.2. Within these ranges, the amount of unreacted iso-butene and the amount of impurities contained in the reactors are reduced, whereby the amount of thermal energy used in the reaction distillation column may be reduced. Here, the volume of each of the reactors 1 may be 10 to 80 $m^3$, or 20 to 70 $m^3$. The volume is preferably 25 to 70 $m^3$.

For example, when the first reaction part includes three or more rectors connected in parallel, a flow ratio of a recycle to a fresh feed may be greater than 3.1 and less than 9.8, or 2.5 to 6.5. The flow ratio is preferably 3.1 to 6.5, more preferably 4.8 to 6.2. Within these ranges, a conversion rate to iso-butene may increase and the amount of impurities may be reduced, whereby a reflux amount in the reaction distillation column may be reduced. As a result, the amount of thermal energy used in the reaction distillation column may be reduced. Here, the volume of each of the reactors may be 10 to 40 $m^3$ or 20 to 35 $m^3$. The volume is preferably 25 to 35 $m^3$.

The second reaction part may include one or more reactors connected in series to the first reaction part.

For example, the second reaction part may include one reactor; or two or more reactors connected in series or in parallel.

Alternatively, the second reaction part may include, for example, one reactor or two to five reactors connected in series. In consideration of process efficiency, the second reaction part preferably includes one reactor.

In the reaction step, a molar ratio of methanol to iso-butene may be, for example, 3:1 to 1:3 or 2:1 to 1:2. The molar ratio is preferably 1.5:1 to 1:1.5. Within these ranges, a conversion rate to iso-butene may be increased while sufficiently lowering reaction temperature. In addition, by-products are reduced and costs for separating methanol are reduced, which is economical.

A flow rate of the fresh feed fed into the first reaction part may be, for example, 10 to 60 ton/hr, or 15 to 55 ton/hr. The flow rate is preferably 20 to 50 ton/hr. When operation is performed within these ranges, a conversion rate to iso-butene may be increased and the amount of impurities may be lowered.

A total volume of the one or more reactors included in the first reaction part may be, for example, 10 to 150 $m^3$, or 15 to 130 $m^3$. The total volume is preferably 20 to 125 $m^3$. Within these ranges, a conversion rate to iso-butene may be increased and the amount of impurities may be reduced, whereby the amount of thermal energy used in the reaction distillation column may be reduced.

For example, when the first reaction part includes one reactor, the volume of the reactor may be 10 to 120 $m^3$, or 20 to 105 $m^3$. Preferably, the volume is 25 to 105 $m^3$. Within these ranges, a conversion rate to iso-butene may be increased and the amount of impurities may be reduced, whereby a reflux amount in the reaction distillation column may be reduced.

As another embodiment, when the first reaction part includes two reactors connected in parallel, the volume of each of the reactors may be 10 to 80 $m^3$, or 20 to 70 $m^3$. Preferably, the volume is 25 to 70 $m^3$. Within these ranges, a conversion rate to iso-butene may be increased and the amount of impurities may be reduced, whereby a reflux amount in the reaction distillation column may be reduced.

As another example, when the first reaction part includes three reactors connected in parallel, the volume of each of the reactors may be 10 to 40 $m^3$ or 20 to 35 $m^3$. The volume is preferably 25 to 35 $m^3$. Within these ranges, a conversion rate to iso-butene may be increased and the amount of impurities may be reduced, whereby a reflux amount in the reaction distillation column may be reduced.

The reactors may be used without specific limitation so long as they are commonly used in the technical field to which the present invention pertains. The reactors may be, for example, fixed bed reactors.

The temperature of the stream introduced to the first reaction part may be, for example, 20 to 80° C. or 30 to 70° C. The temperature is preferably 35 to 60° C. Within these ranges, a conversion rate to iso-butene may be increased.

In addition, the temperature of the stream introduced to the second reaction part may be, for example, 20 to 80° C. or 30 to 70° C. The temperature is preferably 35 to 60° C. Within these ranges, a conversion rate to iso-butene may be increased.

Each of the first reaction part and the second reaction part may further include, for example, a flow rate control valve provided to a raw material introduction pipe of each thereof.

The flow rate control valve may be used without specific limitation so long as it is generally used in the technical field.

A conversion rate to iso-butene in the first reaction part may be, for example, 40 to 99%, or 45 to 98% The conversion rate is preferably 50 to 95%. In this case, the amount of thermal energy used in the reaction distillation column may be reduced.

A conversion rate to iso-butene in the second reaction part may be, for example, 50 to 99%, or 55 to 98%. The conversion rate is preferably 60 to 95%. In this case, the amount of thermal energy used in the reaction distillation column may be reduced.

The conversion rate to iso-butene, for example, may be analyzed by gas chromatography and may be calculated according to Equation 1 below:

Conversion rate (%)=(Moles of reacted iso-butene)/(moles of supplied iso-butene)×100   [Equation 1]

Reaction temperature in the reaction step may be, for example, 20 to 80° C., or 35 to 75° C. The reaction temperature is preferably 35 to 70° C. Reaction pressure in the reaction step may be, for example, 0.5 to 15 kgf/cm$^2$-g, or 2 to 14 kgf/cm$^2$-g. The reaction pressure is preferably 5 to 13 kgf/cm$^2$-g. Within these ranges, a conversion rate to iso-butene may be increased.

As a particular example, reaction temperature in the first reaction part may be 20 to 80° C. or 30 to 70° C. The reaction temperature is preferably 35 to 65° C. Within these ranges, reaction rate is excellent, and equilibrium reaction favorable to a product proceeds.

As a particular example, reaction temperature in the second reaction part may be 20 to 80° C., or 30 to 70° C. The reaction temperature is preferably 35 to 60° C., more preferably 42 to 47° C.

Within these ranges, a reaction rate is excellent, and equilibrium reaction favorable to a product proceeds.

As a particular example, reaction pressure in the first reaction part may be, for example, 0.5 to 15 kgf/cm$^2$-g, 2 to 14 kgf/cm$^2$-g. The reaction pressure is preferably 4 to 13 kgf/cm$^2$-g, more preferably 4 to 8 kgf/cm$^2$-g. Within these ranges, a conversion rate to iso-butene may be increased.

As a particular example, reaction pressure in the second reaction part may be, for example, 0.5 to 15 kgf/cm$^2$-g, 2 to 14 kgf/cm$^2$-g. The reaction pressure is preferably 5 to 13 kgf/cm$^2$-g, more preferably 5 to 8 kgf/cm$^2$-g. Within these ranges, a conversion rate to iso-butene may be increased.

The acid catalyst charged in the reaction distillation column may be, for example, an acidic cation resin.

The acidic cation resin may be used without specific limitation so long as it is generally used in the technical field.

For example, the acidic cation resin may contain a sulfonic acid group and may include a substance obtained by polymerizing or co-polymerizing an aromatic vinyl compound and then sulfonating the same.

The aromatic vinyl compound may be, for example, one or more selected from the group consisting of styrene, vinyl toluene, vinyl naphthalene, vinyl ethylbenzene, methyl styrene, vinyl chlorobenzene, and vinyl xylene.

In addition, during the polymerization or co-polymerization, for example, a crosslinking agent, such as divinyl benzene, divinyl toluene, or divinyl phenyl ether, may be further included.

The acidic cation resin may be prepared, for example, in the presence or absence of a solvent or a dispersant. Here, a polymerization initiator may be, for example, an inorganic or organic peroxide, persulfate, or the like.

The acidic cation resin may be, for example, the same as the acid ion exchange resin used in the reaction parts.

For example, the reaction product obtained from the reaction step is preferably introduced below the packing stage of the reaction distillation column and in a direction closer to a reboiler, which may prevent poisoning of the catalyst due to metal ions that may be present in a stream introduced to the reaction distillation column and may prevent catalyst damage by preventing overheating that may occur in a lower section of the reaction distillation column.

The reboiler may be a heat exchanger generally used in the art. The reboiler may be, for example, a vertical circulation-type heat exchanger.

The reaction distillation column may include, for example, 1 to 40 packing stages or 5 to 25 packing stages. The reaction distillation column preferably includes 5 to 20 packing stages. Within these ranges, the concentration of methyl tert-butyl ether in a stream at a lower part of the reaction distillation column may be further increased.

In addition, the reaction distillation column may further include an additional packing stage so as to further lower the concentration of iso-butene in a stream at an upper part of the reaction distillation column.

Methanol may be additionally fed into a packing stage of the reaction distillation column or an upper or lower part of the reaction distillation column. Accordingly, the concentration of methyl tert-butyl ether in a stream at a lower part of the reaction distillation column may be further increased.

In addition, an average temperature of the packing stage may be 55° C. to 70° C. The average temperature is particularly preferably 58° C. to 67° C.

In the purification step, a reflux ratio in the reaction distillation column may be, for example, 0.5 to 1.3, or 0.6 to 1.2. Preferably, the reflux ratio is 0.7 to 0.95. Within these ranges, the concentration of methyl tert-butyl ether in a stream at a lower part of the reaction distillation column may be 98% by weight or more, the concentration of iso-butene in a stream at an upper part thereof may be less than 200 ppm, and a use amount of thermal energy may be reduced.

The expression "reflux ratio," as used in the present invention, refers to a ratio of refluxed flow to flow discharged from the reaction distillation column.

In addition, in accordance with the present invention, the reflux ratio may be lowered, whereby the amount of stream used may be considerably reduced. Accordingly, the amount of thermal energy used in the reaction distillation column may be reduced.

The temperature of the reaction product introduced to the reaction distillation column may be, for example, 40 to ° C., and the pressure thereof may be, for example, 0.5 to 10 gf/cm$^2$-g.

In particular, a preferred introduction temperature of the reaction distillation column is, for example, 60 to 75° C. Within these ranges, a conversion rate to iso-butene may be increased and impurities may be reduced, whereby the amount of thermal energy used in the reaction distillation column may be reduced.

In particular, the pressure of the reaction distillation column may be, for example, 4 to 10 kgf/cm$^2$-g. The pressure is preferably 4 to 6 kgf/cm$^2$-g. Within these ranges, a conversion rate to iso-butene may be increased and impurities may be reduced, whereby the amount of thermal energy used in the reaction distillation column may be reduced.

A stream discharged from an upper part of the reaction distillation column may include, for example, 1% by weight or less, or 0.8% by weight or less of iso-butene. The stream preferably includes 0.6% by weight or less of iso-butene. Within these ranges, a reflux amount in the reaction distillation column may be reduced, whereby the amount of thermal energy used in the reaction distillation column may be reduced.

A stream discharged from a lower part of the reaction distillation column may include, for example, 50 to 99.9% by weight or more, or 90 to 99.9% by weight of methyl tert-butyl ether. The stream preferably includes 98 to 99.9% by weight of methyl tert-butyl ether.

Since methyl tert-butyl ether obtained from the stream, which is discharged from a lower part of the reaction distillation column, contains only a very small amount of methyl sec-butyl ether (MSBE), it may be suitable for production of high-purity iso-butene by re-decomposition.

In the purification step, the amount of thermal energy used in the reaction distillation column may be, for example, less than 0.99, 0.80 to 0.95, or 0.88 to 0.94, based a reference process.

The amount of the thermal energy used may be determined, for example, based on the amount of thermal energy used in the reaction distillation column under a reference process operation condition illustrated in FIG. 3 (see Example 5), and may be calculated according to Equation 2 below:

Thermal energy use amount=[Amount of thermal energy used in distillation column during operation of process including reactors additionally connected in parallel]/[amount of thermal energy used in reaction distillation column under reference process operation condition]    [Equation 2]

The amount of the used thermal energy may be measured by a method generally used in the art and may be determined by, for example, the flow rate, temperature, and pressure of a stream introduced to the reboiler of the reaction distillation column.

Figure 2:
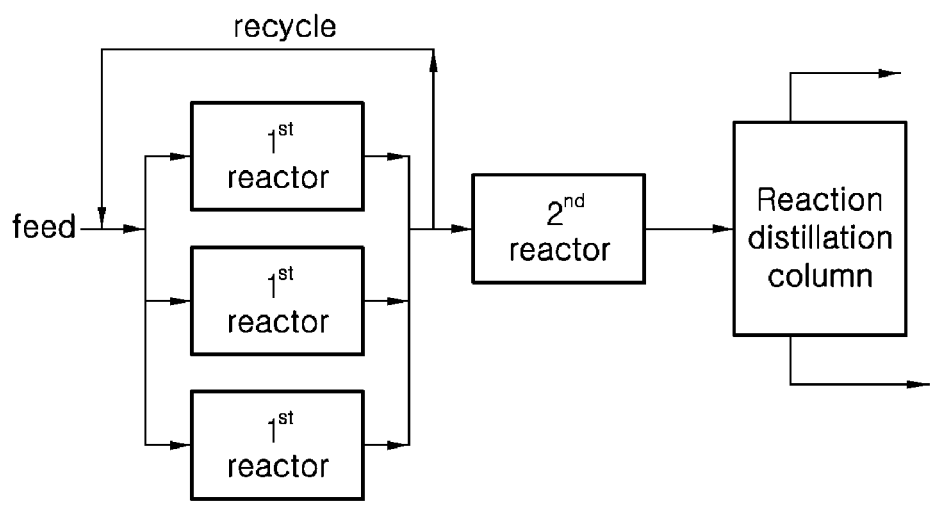
FIG. 2 is a block diagram schematically illustrating process operation of an apparatus wherein a first reaction part including three reactors connected in parallel and a second reaction part including one reactor are connected in series according to an embodiment of the present invention.
Figure 3:
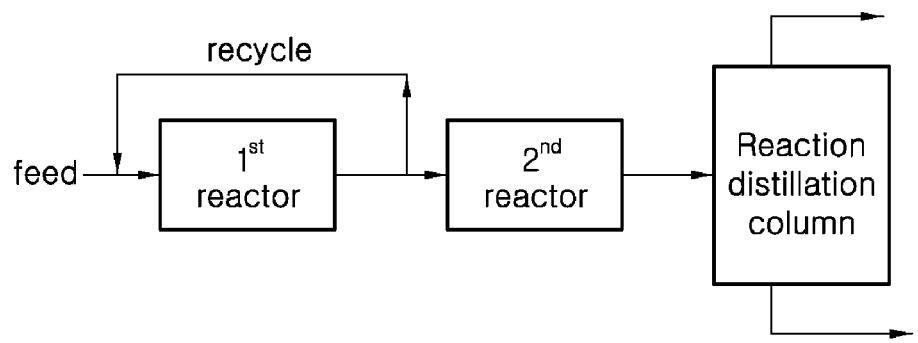
FIG. 3 is a block diagram schematically illustrating process operation of an apparatus wherein a first reaction part including one reactor and a second reaction part including one reactor are connected in series according to an embodiment of the present invention.
Figure 4:
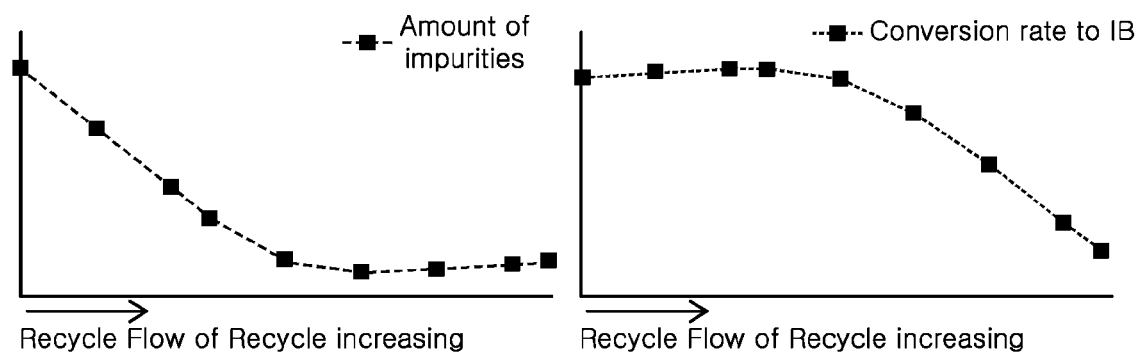
FIG. 4 is graphs illustrating the amount of impurities and a conversion rate to iso-butene dependent upon increase in recycle flow.

Meanwhile, apparatuses used in the method of preparing methyl tert-butyl ether of the present invention are preferably apparatuses illustrated in FIGS. 1 to 3, but the present invention is not limited thereto.

For example, an apparatus used in the method of preparing methyl tert-butyl ether may include a raw material supply pipe 1 configured to introduce a first stream including iso-butene and methanol to a first reaction part, the first reaction part including two reactors connected in parallel, a second reaction part including one reactor connected in series to the first reaction part, a recycle pipe 2 configured to recycle a portion of a reaction product discharged from the first reaction part to the first reaction part, and a reaction distillation column connected to the second reaction part, as illustrated in FIG. 1.

As another example, an apparatus used in the method of preparing methyl tert-butyl ether may include a raw material supply pipe 1 configured to introduce a first stream including iso-butene and methanol to a first reaction part, the first reaction part including three reactors connected in parallel, a second reaction part including one reactor connected in series to the first reaction part, a recycle pipe 2 configured to recycle a portion of a reaction product discharged from the first reaction part to the first reaction part, and a reaction distillation column connected to the second reaction part, as illustrated in FIG. 2.

As another example, an apparatus used in the method of preparing methyl tert-butyl ether may include a raw material supply pipe 1 configured to introduce a first stream including iso-butene and methanol to a first reaction part, the first reaction part including one reactor, a second reaction part including one reactor connected in series to the first reaction part, a recycle pipe 2 configured to recycle a portion of a reaction product discharged from the first reaction part to the first reaction part, and a reaction distillation column connected to the second reaction part, as illustrated in FIG. 3.

In addition, a mixer configured to mix ingredients to be included in the first stream, before the ingredients are introduced in the reactor, may be further installed at a front end of the first reaction part.

In addition, a pre-heater may be installed at a front end of the first reaction part, and a cooler may be installed at a rear end of the first reaction part.

Further, pipelines configured to respectively introduce ingredients in the first stream to the first reaction part may be included, or a plurality of pipelines which are branched from one pipeline directly connected to the reactor and into which ingredients included in the first stream are respectively fed may be included.

Meanwhile, the first stream (fresh feed) including iso-butene and methanol introduced through the raw material supply pipe 1; and a third stream mixed with a second stream (recycle) that is introduced through a recycle pipe 2 and includes a portion of the reaction product discharged from the first reaction part are fed into the first reaction part. Here, a flow ratio of the recycle to the fresh feed may be dependent upon a total volume of the reactors included in the first reaction part.

For example, a flow ratio of a recycle to a fresh feed may be greater than 0.9 and less than 1.7 when a total volume of the one or more reactors included in the first reaction part is 30 m$^3$ or less, a flow ratio of a recycle to a fresh feed may be greater than 2.2 and less than 4.8 when a total volume of the one or more reactors included in the first reaction part is greater than 30 m$^3$ and 60 m$^3$ or less, and a flow ratio of a recycle to a fresh feed may be greater than 3.1 and less than 9.8 when a total volume of the one or more reactors included in the first reaction part is greater than 60 m$^3$. In this case, a conversion rate to iso-butene may increase and the amount of impurities may be reduced, whereby a reflux amount in the reaction distillation column may be reduced. As a result, the amount of thermal energy used in the reaction distillation column may be reduced.

A portion of a reaction product discharged from the first reaction part is fed into the second reaction part. Preferably, a conversion rate to iso-butene in the reaction product discharged from the second reaction part is, for example, 90 to 96%.

In addition, the reaction product discharged from the second reaction part may be introduced to the reaction distillation column through the pipelines, a stream including 200 ppm or less of iso-butene may be discharged from an upper part of the reaction distillation column, and a stream including 50 to 99.9% by weight, preferably 98% by weight or more, of methyl tert-butyl ether may be discharged from a lower part of the reaction distillation column.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLES

Example 1

Referring to the accompanying FIG. 1 below, the volume of each of the reactors included in the first reaction part was 30 m$^3$, two reactor each charged with 600 kg of a catalyst per unit volume (m$^3$) of each thereof and connected in parallel (a total volume of the reactors was 60 m$^3$), a fresh feed ingredient was iso-butane, iso-butene, 1-butene, 1,3 butadiene, n-butane, tert-2-butene, cis-2 butene, 1,2 butadiene, or a C5 carbon compound, a flow rate was 41.7 ton/hr, and a recycle ingredient included the fresh feed ingredient and methyl tert-butyl ether.

In addition, methanol having a purity of 99.9% or more was introduced to the reactor through a separate pipe such that a molar ratio of methanol to iso-butene became 1:1.03.

A flow ratio of a recycle to a fresh feed was 2.6, reaction in the first reaction part was carried out under conditions such as an addition temperature of 37° C., a temperature inside the reactors of 37 to 65° C., and a pressure of 4.7 to 5.0 kgf/cm$^2$-g, and reaction in the second reaction part was carried out under conditions such as an addition temperature of 42° C., a temperature inside the reactor of 42 to 47° C., and a pressure of 6.3~6.7 kgf/cm$^2$-g.

Subsequently, purification was carried out using a distillation column including 13 packing stages, which included a strongly acidic cation resin, as a fixed layer, under conditions such as an introduction temperature of the distillation column of 75° C., an average temperature of the packing stages of 57 to 60° C., and a pressure of 5.6 to 5.9 kgf/cm$^2$-g. As a result, methyl tert-butyl ether was prepared.

Example 2

An experiment was carried out in the same manner as in Example 1, except a flow ratio of a recycle to a fresh feed was 3.1.

Example 3

An experiment was carried out in the same manner as in Example 1, except that three reactors, the volume of each of which was 30 m$^3$, were connected in parallel to a first reaction part (a total volume of the reactors was 90 m$^3$) as illustrated in FIG. 2, and a flow ratio of a recycle to a fresh feed was 4.8.

Example 4

An experiment was carried out in the same manner as in Example 1, except that three reactors, the volume of each of which was 30 m$^3$, were connected in parallel to a first reaction part (a total volume of the reactors was 90 m$^3$) as illustrated in FIG. 2, and a flow ratio of a recycle to a fresh feed was 6.2.

Example 5

An experiment was carried out in the same manner as in Example 1, except that one reactor having a volume of 30 m$^3$ was included in a first reaction part (a total volume of the reactor was 30 m$^3$) as illustrated in FIG. 3, and a flow ratio of a recycle to a fresh feed was 1.4.

The amount of thermal energy used in the reaction distillation column in this case was used as a reference.

Comparative Example 1

An experiment was carried out in the same manner as in Example 1, except that a flow ratio of a recycle to a fresh feed was 2.2.

Comparative Example 2

An experiment was carried out in the same manner as in Example 1, except that a flow ratio of a recycle to a fresh feed was 4.8.

Comparative Example 3

An experiment was carried out in the same manner as in Example 3, except that a flow ratio of a recycle to a fresh feed was 3.1.

Comparative Example 4

An experiment was carried out in the same manner as in Example 3, except that a flow ratio of a recycle to a fresh feed was 9.8.

Comparative Example 5

An experiment was carried out in the same manner as in Example 5, except that a flow ratio of a recycle to a fresh feed was 0.9.

Comparative Example 6

An experiment was carried out in the same manner as in Example 5, except that a flow ratio of a recycle to a fresh feed was 1.7.

In each of Examples 1 to 5 and Comparative Examples 1 to 6, a conversion rate to iso-butene was about 99.7%, the content of iso-butene in a stream at an upper part of the reaction distillation column was 200 ppm or less, and the content of MTBE in a stream at a lower part of the reaction distillation column was 98.8% by weight or more.

Test Example

A thermal energy use amount according to process operation of each of Examples 1 to 5 and Comparative Examples 1 to 6 was calculated by the following manner. Results are summarized in Table 1 below.

Thermal energy use amount: The amount of thermal energy used in the reaction distillation column according to the process operation of Example 5 (FIG. 3 below) was determined as a reference, and the thermal energy use amount was calculated according to the following Equation 2:

Thermal energy use amount=[Amount of thermal energy used in reaction distillation column during operation of process including reactors additionally connected in parallel]/[amount of thermal energy used in reaction distillation column under reference process operation condition]  [Equation 2]

TABLE 1

| Classification | Example 1 | Example 2 | Example 3 | Example 4 | Example 5 | Comparative Example 1 | Comparative Example 2 | Comparative Example 3 | Comparative Example 4 | Comparative Example 5 | Comparative Example 6 |
|---|---|---|---|---|---|---|---|---|---|---|---|
| Flow rate of recycle/fresh feed | 2.6 | 3.1 | 4.8 | 6.2 | 1.4 | 2.2 | 4.8 | 3.1 | 9.8 | 0.9 | 1.7 |

TABLE 1-continued

| Classification | Example 1 | Example 2 | Example 3 | Example 4 | Example 5 | Comparative Example 1 | Comparative Example 2 | Comparative Example 3 | Comparative Example 4 | Comparative Example 5 | Comparative Example 6 |
|---|---|---|---|---|---|---|---|---|---|---|---|
| Thermal energy use amount | 0.94 | 0.90 | 0.88 | 0.91 | 1 | 1.03 | 1.02 | 1.03 | 1.00 | 1.04 | 1.06 |
| Reflux ratio of reaction distillation column | 1.01 | 0.93 | 0.90 | 0.96 | 1.14 | 1.18 | 1.22 | 1.17 | 1.18 | 1.21 | 1.29 |

As shown in Table 1, it can be confirmed that, in the case of Examples 1 and 2 in which a total volume of the one or more reactors included in the first reaction part is 60 m³ and a flow ratio of a recycle to a fresh feed is 2.4 to 4, the amount of thermal energy used is greatly decreased, compared to Comparative Examples 1 and 2 in which a flow ratio of a recycle to a fresh feed is 2.2 or 4.8.

In addition, it can be confirmed that, in the case of Examples 3 and 4 in which a total volume of the reactors included in the first reaction part is 90 m³ and a flow ratio of a recycle to a fresh feed is 4.8 to 6.2, the amount of thermal energy used is greatly decreased, compared to Comparative Examples 3 and 4 in which a flow ratio of a recycle to a fresh feed is 3.1 or 9.8.

Further, it can be confirmed that, in the case of Example 5 in which a total volume of the reactor included in the first reaction part is 30 m³ and a flow ratio of a recycle to a fresh feed is 1.4, thermal energy is greatly decreased, compared to Comparative Examples 5 and 6 in which a flow ratio of a recycle to a fresh feed is 0.9 or 1.7.

The invention claimed is:

1. A method of preparing methyl tert-butyl ether, the method comprising:
    a reaction step of reacting methanol with iso-butene in presence of an acid catalyst to generate methyl tert-butyl ether; and
    a purification step of purifying the reaction product obtained by the reaction step by introducing the reaction product into a reaction distillation column comprising a packing stage containing an acid catalyst,
    wherein the reaction step is performed in a first reaction part comprising two or more reactors connected in parallel, and in a second reaction part comprising one or more reactors connected in series to the first reaction part,
    wherein a portion of a reaction product discharged from the first reaction part is recycled in the first reaction part as a recycle feed, wherein:
    a flow ratio of the recycle feed to a fresh feed is greater than 0.9 and less than 1.7 when a total volume of the two or more reactors comprised in the first reaction part is 30 m³ or less, or
    flow ratio of a recycle to a fresh feed is greater than 2.2 and less than 4.8 when a total volume of the two or more reactors comprised in the first reaction part is greater than 30 m³ and 60 m³ or less, or
    a flow ratio of the recycle feed to a fresh feed is greater than 3.1 and less than 9.8 when a total volume of the two or more reactors comprised in the first reaction part is greater than 60 m³.

2. The method according to claim 1, wherein the acid catalyst is comprised in an amount of 200 to 1200 kg per unit volume (m³) of the each reactor.

3. The method according to claim 1, wherein, in the reaction step, a molar ratio of methanol to iso-butene is in a range of 3:1 to 1:3.

4. The method according to claim 1, wherein the fresh feed fed into the first reaction part comprises a mixture of C4-hydrocarbon comprising 20 to 60% by weight of iso-butene.

5. The method according to claim 1, wherein a flow rate of the fresh feed fed into the first reaction part is 10 to 60 ton/hr.

6. The method according to claim 1, wherein the recycle feed fed into the first reaction part comprises 1 to 20% by weight of iso-butene, 1 to 20% by weight of methanol, and 20 to 60% by weight of methyl tert-butyl ether.

7. The method according to claim 1, wherein a total volume of the two or more reactors comprised in the first reaction part is 10 to 150 m³.

8. The method according to claim 1, wherein a conversion rate to iso-butene in the second reaction part is 50 to 99%.

9. The method according to claim 1, wherein the reaction step is performed at a reaction temperature of 20 to 80° C. under a reaction pressure of 0.5 to 15 kgf/cm²-g.

10. The method according to claim 1, wherein the reaction distillation column comprises 1 to 40 packing stages.

11. The method according to claim 1, wherein the acid catalyst charged in the reaction distillation column is an acidic cation resin.

12. The method according to claim 1, wherein the reaction product is introduced at an introduction temperature of 40 to 90° C. under a pressure of 0.5 to 10 kgf/cm2-g into the reaction distillation column.

13. The method according to claim 1, wherein a stream discharged from an upper part of the reaction distillation column comprises 1% by weight or less of iso-butene.

14. The method according to claim 1, wherein a stream discharged from a lower part of the reaction distillation column comprises 50 to 99.9% by weight of methyl tert-butyl ether.

* * * * *